United States Patent [19]

Saito et al.

[11] Patent Number: 4,607,521
[45] Date of Patent: Aug. 26, 1986

[54] METHOD OF IMPROVING RESPONSE CHARACTERISTICS OF GAS SENSOR USING MICROWAVE SPECTROMETER

[75] Inventors: Tomoo Saito; Mitsutoshi Tanimoto; Masayoshi Yasuda, all of Kanagawa; Yasuharu Ijuin, Tokyo; Akio Hikita, Kanagawa; Naotake Morikawa, Tokyo; Hiromichi Uehara, Saitama; Masaru Fukuyama, Tokyo, all of Japan

[73] Assignee: Sagami Chemical Research Center, Tokyo, Japan

[21] Appl. No.: 673,456

[22] Filed: Nov. 20, 1984

[51] Int. Cl.[4] .............................................. G01N 22/00
[52] U.S. Cl. ................................... 73/23; 324/58.5 C
[58] Field of Search ................................. 73/23, 23.1; 324/58.5 C, 58.5 R

[56] References Cited

U.S. PATENT DOCUMENTS 3,805,148 4/1974 Uehara et al. ............... 324/58.5 C
3,973,186 8/1976 Uehara et al. ............... 324/58.5 C

OTHER PUBLICATIONS

H. H. Hausdorff, Vapor Fractometry (Gas Chromatography)-A Powerful New Tool in Chemical Analysis, The Perkin-Elmer Corp., p. 22, Sep. 1955.

Primary Examiner—Stephen A. Kreitman
Attorney, Agent, or Firm—Sughrue, Mion, Zinn Macpeak & Seas

[57] ABSTRACT

A response characteristics of a microwave spectroscopic measuring system is remarkably improved by supplying a carrier to a continuously flowing sample containing a polar substance to be measured quantitatively. The carrier contains a compound having at least similar chemical form to that of the polar substance.

4 Claims, 10 Drawing Figures

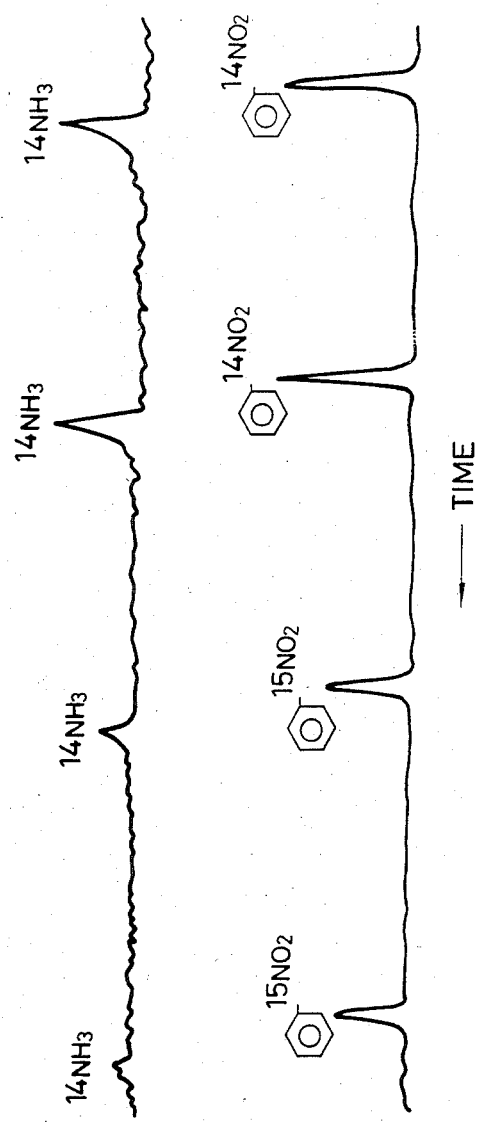

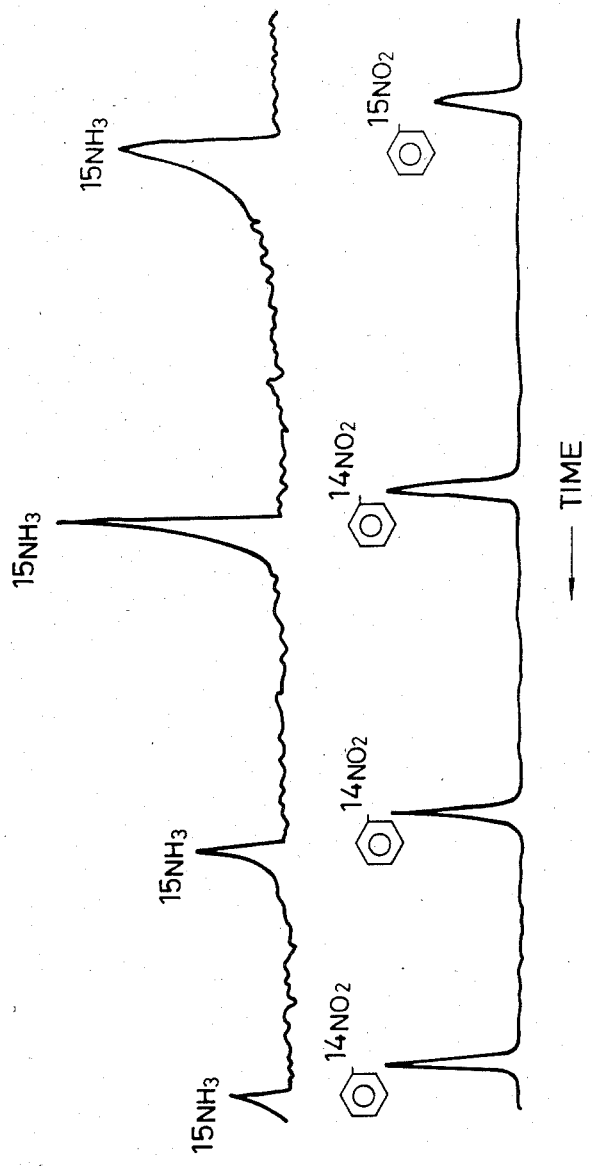

METHOD OF IMPROVING RESPONSE CHARACTERISTICS OF GAS SENSOR USING MICROWAVE SPECTROMETER

BACKGROUND OF THE INVENTION

The present invention relates to a method of improving the response characteristics of a continuous gas sensor using a microwave spectrometer and, particularly, to such a method whereby continuous measurement of stable isotopes is made possible.

It has been known that the conventional gas sensor utilizing a microwave spectrometer is generally large in size and expensive to manufacture and the handling thereof is relatively difficult.

In view of these facts, an improvement has been proposed to the conventional gas sensor of this type which includes a resonant cavity sample cell and a solid-state microwave oscillator (instead of the conventional klystron), resulting in a gas sensor which is compact in size, inexpensive to manufacture and more sensitive than the conventional sensor.

In the practical use of such gas sensor, however, problems have been uncovered. Particularly, substances to be detected by the microwave spectrometer are polar molecules having a significant vapor pressure. Examples of such polar molecules include nitrogen compounds such as $NH_3$, $N_2O$ and $NO_2$, sulfur compounds such as $SO_2$, $CH_3SH$ and $COS$, aldehydes such as $HCHO$ and $CH_3CHO$, and other molecules such as $H_2O$. These molecules tend to be adsorbed on walls of the constituent components of the gas sensor with which these molecules contact. This adsorption may lengthen the response time of the gas sensor for variations of concentration of the substance.

FIG. 1 illustrates this fact. In FIG. 1, $NH_3$ of 20 ppm (the polar molecule) is supplied to the gas sensor. FIG. 1 shows an output signal obtained from the gas sensor. As is clear from FIG. 1, a 90% indication is obtained after 10 minutes from injection of $NH_3$ of 20 ppm, and a 100% indication, i.e., 20 ppm, is obtained after about 40 minutes from the sample injection. That is, even with this improved gas sensor, it is impossible to use it as a sensor for continuous measurement of minute amounts of polar molecules whose concentration varies rapidly. In other words, in other to quantitatively measure a sample immediately after the injection thereof, it is necessary to inject an increased amount of the sample to the senor, resulting in a substantial degradation of the sensitivity of the instrument.

This problem becomes more severe when polar molecules to be measured contain stable isotopes and are injected successively in gas form from an apparatus such as a gas chromatography apparatus. For example, when polar components contained in the injected material from a gas chromatography apparatus are converted by a preprocessing unit to a chemical form suitable for use in microwave spectroscopic measurement and supplied successively to the sensor, it may become impossible to measure them precisely because one of the components supplied thereto affects the measurement of the components supplied thereto subsequently.

FIGS. 2A and 2B are graphs depicting this fact. In FIG. 2A, $^{14}N$-nitrobenzene and $^{15}N$-nitrobenzene are supplied successively to a preprocessing unit containing Ni as a catalyst to convert them into $^{14}NH_3$ and $^{15}NH_3$ by hydrogenation, and nitrogen isotope labelled ammonia molecules are supplied successively to a sensor tuned to 23,870 MHz, which is the resonant frequency of $^{14}NH_3$.

As is clear from FIG. 2A, $^{14}NH_3$ is measured in response to a first injection of $^{14}N$-nitrobenzene and is also measured in response to a second injection of $^{14}N$-nitrobenzene. So long as the second injection is concerned, it is also measured although there is a considerable tailing of the detected waveform. However, when $^{15}N$-nitrobenzene is injected thereafter, $^{14}NH_3$ is still measured. This phenomenon is repeated for subsequent injections of $^{15}N$-nitrobenzene.

In FIG. 2B, $^{15}NH_3$ is measured, in the same manner as described with reference to FIG. 2A, by setting the resonance frequency of the microwave sensor at 22,789 MHz. The result is similar to that shown in FIG. 2A.

In order to resolve these problems, it may be effective to constitute at least the wall portions of the measuring system which the samples contact with a material whose adsorptivity for the sample is low and/or to reduce the total area of the wall portions substantially. Alternatively, it may be effective to maintain the interior of the measuring system under a balanced absorption condition. These approaches, however, are very difficult to realize in practice.

SUMMARY OF THE INVENTION

An object of the present invention is thus to provide a measuring method whereby the response characteristics of a gas sensor using a microwave spectrometer are improved.

Another object of the present invention is to provide a method of continuously measuring concentrations of stable isotopes.

These objects are achieved, according to the present invention, by supplying a carrier containing a compound of a constant concentration to a sample flowing continuously to a spectrometer, a chemical form of the compound being at least similar to that of a component of the sample to be detected to establish, in a measuring system, a condition whereby adsorption of the component and the compound by walls of the measuring system is at least saturated. A microwave spectroscopic measurement is performed under this condition.

BRIEF DESCRIPTION OF THE DRAWINGS

FIGS. 2A and 2B show responses characteristics of the conventional microwave gas sensor for nitrogen isotope labelled compounds;

DESCRIPTION OF THE PREFERRED EMBODIMENTS

Figure 3:
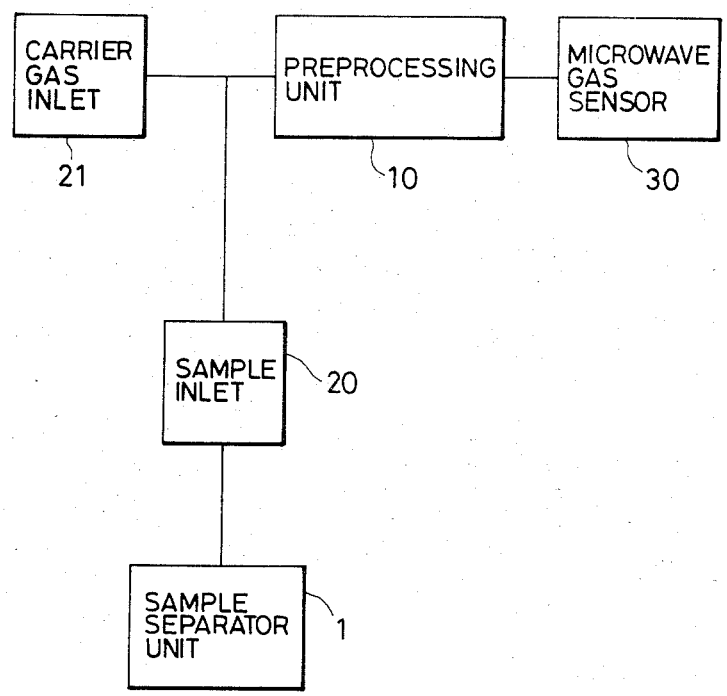
FIG. 3 shows schematically an example of a measuring system for carrying out the present invention.

FIG. 3 shows schematically an apparatus implementing the present invention. A sample separator unit 1 is connected to a sample inlet 20, and an output of the sample inlet 20 is added with a carrier gas from a carrier gas inlet 21 as passed to a sample preprocessing unit 10 having an output connected to a microwave gas sensor 30.

The sample preprocessing unit 10 functions to convert a sample into a compound having a chemical form acceptable for the microwave gas sensor 30, and the carrier inlet 21 functions to introduce a carrier gas of a constant concentration containing the same or similar compound or compounds to that of the sample, for instance, $NH_3$ or methylamine when $^{14}NH_3$ and/or $^{15}NH_3$ is to be measured with the measuring system. The conversion of the sample to such compound may be performed by oxidative decomposition or hydrogenation in the preprocessing unit 10 by using a catalyst according to the following reactions, for example:

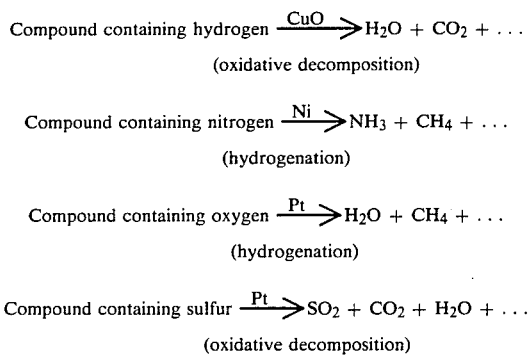

The sample separating unit 1 may be a gas or liquid chromatograph apparatus.

In a case where the sample is volatile, a gas chromatograph apparatus should be used, and in a case where it is necessary to separate the sample in a solution, a liquid chromatograph apparatus is preferable.

The microwave gas sensor 30 has a resonant frequency which may be variable and provides a microwave absorption spectrum of a particular molecule whose inherent frequency coincides with the resonance frequency of the sensor.

In accordance with the invention, the microwave gas sensor 30 uses a resonance cavity as a sample cell and a solid-state microwave generator. Preferred embodiments will be described with reference to measurements of $^{14}NH_3$ and $^{15}NH_3$ as examples. A microwave gas sensor disclosed in Japanese Laid Open Patent Application No. 100887/1978 or 197455/1982 may be used for this purpose.

Figure 4:
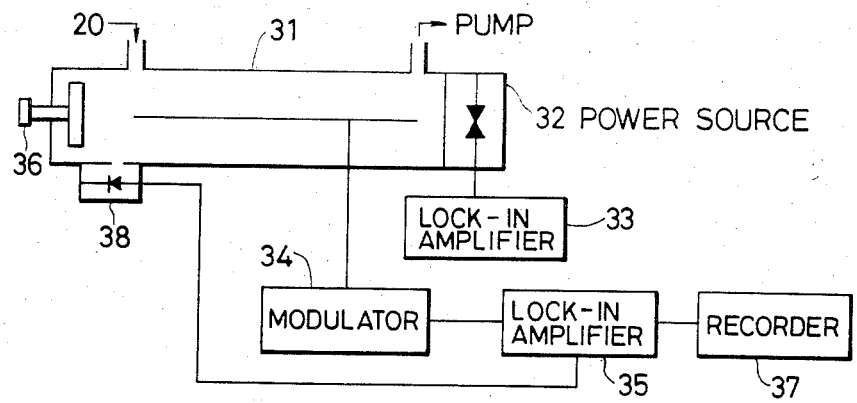
FIGS. 4 and 5 show constructive examples of a microwave spectrometer to be used in the measuring system of FIG. 3.

FIG. 4 shows a microwave gas sensor of the type disclosed in Japanese Laid Open Patent Application No. 100887/1978. The microwave gas sensor includes a parallelopiped Stark resonance cavity 31, a microwave generator 32, a power source 33, a modulator 34, a lock-in amplifier 35, a terminating member 36, a recorder 37 and a detector diode 38. The mode of operation of the sensor is well known.

When $^{15}N$ is measured using the microwave gas sensor shown in FIG. 3, a $^{15}N$ labelled compound (properly called a component) separated from the sample by the same separator 1 is converted into $^{15}NH_3$ by the preprocessing unit 10. In this case, the resonance frequency of the parallelopiped Stark resonator 31 is preliminary set to, for example, 22,789 MHz by adjusting the terminating member 36 of the resonsator 31 so that a peak value of the absorption line of $^{15}NH_3$ at that frequency can be monitored continuously.

Figure 5:
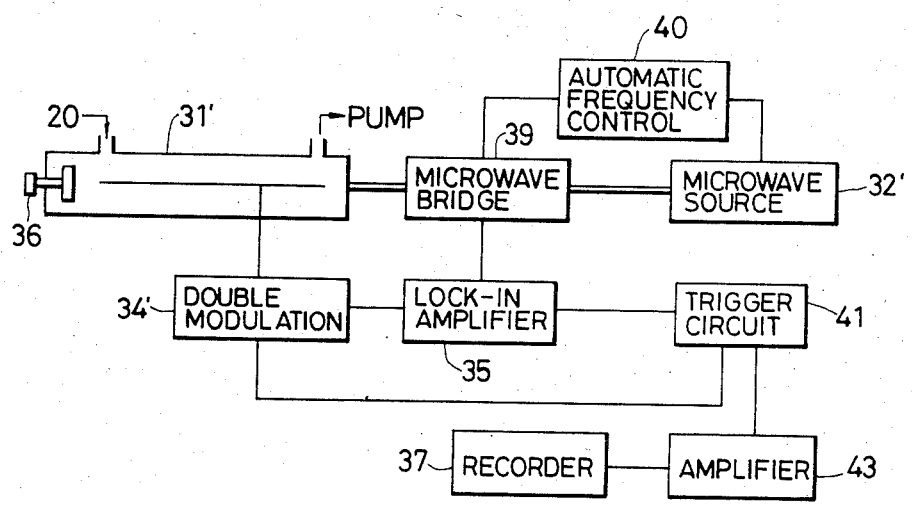

The microwave gas sensor shown in FIG. 5, also used for this purpose, includes a parallelopiped cavity resonator 31', a microwave source 32', a microwave bridge 39, an automatic frequency control (AFC) circuit 40, a double modulator 34', a lock-in amplifier 35, a trigger circuit 41, an amplifier 43 and a recorder 37. The operation thereof is also known well.

In the embodiment shown in FIG. 4 or 5, either $^{14}N$ or $^{15}N$ of components from the sample regulator 1 is measured continuously.

According to the present invention, the response of the microwave gas sensor to rapid changes i concentration of the molecule to be measured is improved by using the carrier gas.

Figure 1:
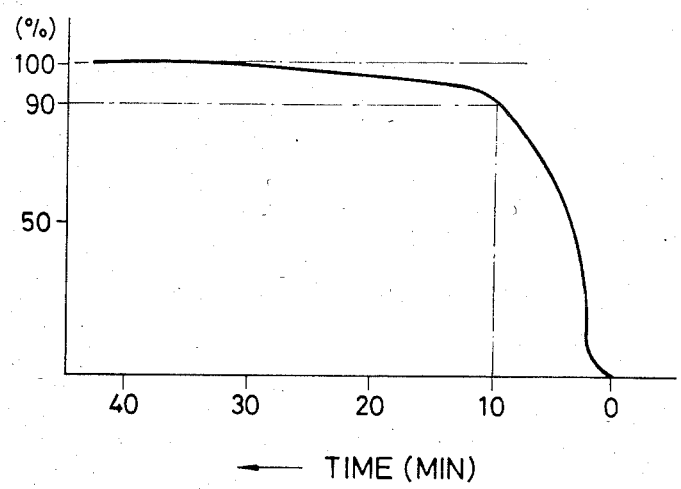
FIG. 1 shows an example of response characteristics of a conventional microwave gas sensor.
Figure 6:
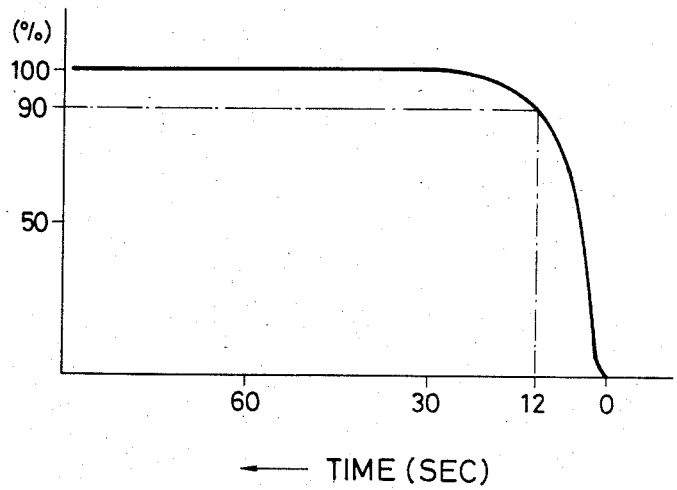
FIG. 6 shows response characteristics of the measuring system according to the present invention.

FIG. 6 shows response characteristics of the measuring system when $NH_3$ of 2,000 ppm is added to the sample as the carrier gas. As shown in FIG. 6, a 90% indication is obtained 12 seconds after injection of the sample, and a 100% indication is obtained after less than 30 seconds from the injection. That is, according to the present invention, the amount of the sample required to measure the sample gas of 20 ppm is about 1/60 that in the case without the carrier gas. This means that the sensitivity of the measurement according to the present invention is 60 times that of the conventional measurement.

In case of measuring ammonia in blood, for example, the amount of blood required to measure ammonia is 3.3 microliters, compared with 200 microliters or more when the conventional method is employed.

Figure 7A:
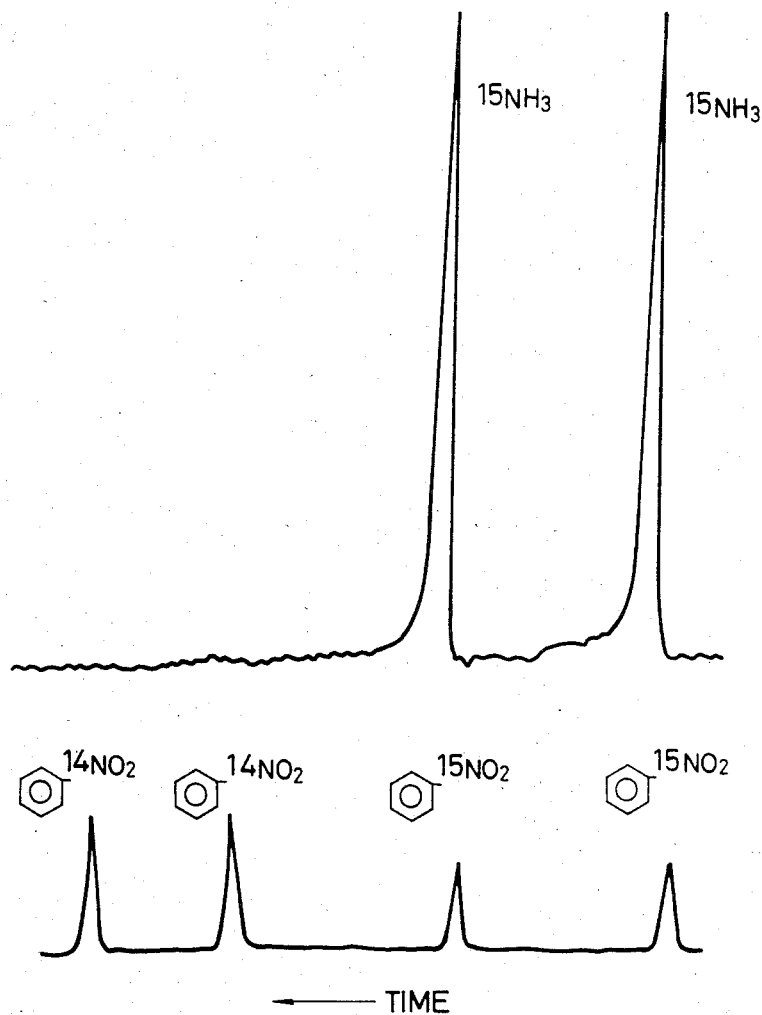
FIGS. 7A and 7B show measurements of $^{14}NH_3$ and $^{15}NH_3$ when a carrier gas is used according to the present invention.
Figure 7B:
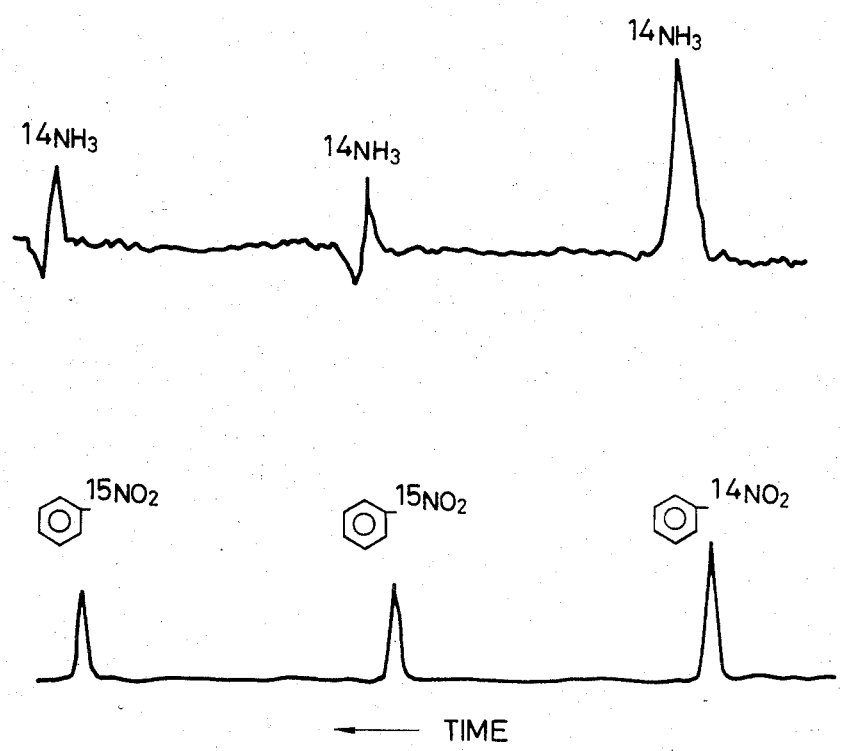

FIGS. 7A and 7B show output patterns of the gas chromatograph apparatus (the sample separator 1) and the microwave gas sensor, when, in the construction shown in FIG. 3, Ni catalyst is provided in the sample preprocessing unit 10 to hydrogenate $^{14}N$-nitrobenzene and $^{15}N$-nitrobenzene applied as the sample and a carrier gas containing $NH_3$ is supplied continuously from the carrier gas inlet 21.

As shown in FIG. 7A, when $^{14}N$-nitrobenzene is injected after $^{15}N$-nitrobenzene of high concentration is measured, there is no detection of $^{15}NH_3$. This means that the exchange between adsorbed $NH_3$ and supplied $NH_3$ in the measuring system becomes negligibly small. Further, as shown in FIG. 7B, when $^{15}N$-nitrobenzene of relatively high concentration is used as the sample, there is a small quasi output corresponding to $^{14}NH_3$ resulting from the exchange. Since, in such a case, an output which is similar in magnitude and opposite in direction to that of the quasi output of $^{14}NH_3$ appears immediately thereafter, this small output can be distinguished from the true output by judging whether or not a quasi signal is present. Alternatively, such a phenomenon can be corrected by correction tables for $^{14}NH_3$ and $^{15}NH_3$ prepared using samples whose $^{15}N$ content is known.

As is clear from FIGS. 7A and 7B, when a continuous flow of $NH_3$ of 2,000 ppm is employed as the carrier, $^{14}NH_3$ or $^{15}NH_3$ from the sample is readily detected due to the reduced possibility of adsorption in the measuring system. Furthermore, even if adsorption occurs, the adsorbed $^{14}NH_3$ or $^{15}NH_3$ is easily exchanged by a large amount of the carrier and discharged again into the measuring system with very little discharged molecules. The adsorption of $^{14}NH_3$ or $^{15}NH_3$ in the measuring system is rendered substantially negligible.

Generally, it is difficult to supply a carrier containing a very small amount of $NH_3$ at a stable concentration. In accordance with the present invention, a carrier gas based on an inert gas such as He, for example, and containing $NH_3$ of 10,000 ppm is stored in a bomb and is added to the sample gas at a ratio of one-fifth of the total amount of the gas flowing through the measuring system. With this method, the stability of the concentration of $NH_3$ of the carrier is remarkably improved. In fact, the stability, as calculated on the basis of the output of the microwave gas sensor, is $\pm 1$ to 2 ppm or less.

Figure 8:
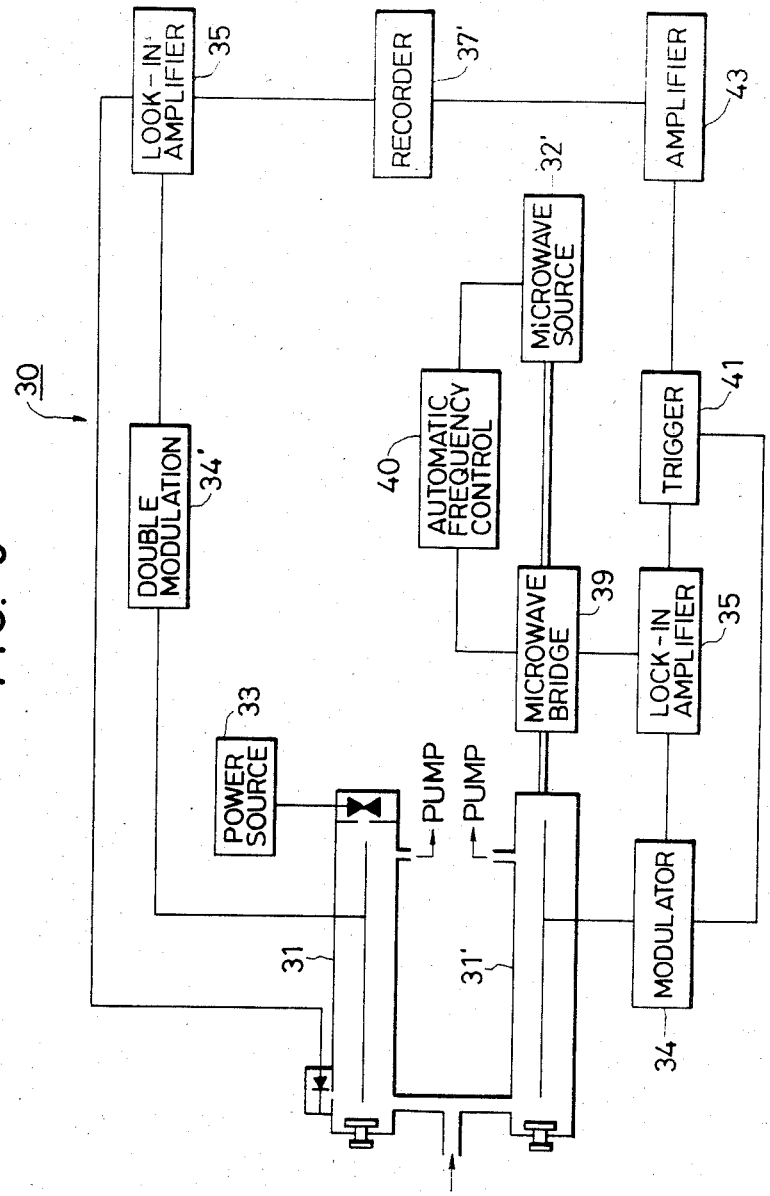
FIG. 8 shows schematically the construction of the measuring system for measuring two isotopes simultaneously.

FIG. 8 shows another example of a microwave gas sensor which may be used in the practice of the present invention and in which both $^{14}NH_3$ and $^{15}NH_3$ are measured simultaneously. In FIG. 8, the sensor used for measuring $^{14}NH_3$ is the sensor 31 shown in FIG. 3 which is tuned to 23,870 MHz, for example. The sensor for $^{15}N$ is the sensor 31' shown in FIG. 5 which is tuned to 22,789 MHz. The sensor 31' may be substituted for the sensor 31. In this embodiment, a sample whose components are separated from each other by the sample separator 1 is passed through the sample preprocessing unit 10 which uses an Ni catalyst as in the previous embodiment to convert $^{15}N$ labelled component into $^{15}NH_3$. The resultant gas is supplied to the sensors 31 and 31' by which $^{14}NH_3$ and $^{15}NH_3$, respectively, are measured.

Although the present invention has been described mainly with reference to ammonia, it can be applied equally well to other polar molecules.

As described above, according to the present invention, the response characteristics of the microwave spectroscopic measuring system are considerably improved so that the system can be used for continuous measurement of minute amounts of polar substances whose concentration may vary rapidly.

We claim:

1. A method of sensing concentrations of a gas sample with a gas sensor using a microwave spectrometer, wherein the improvement comprises continuously supplying to a gas flowing through said gas sensor as a sample to be sensed a first compound having an identical or similar chemical form to that of the sample at a rate at least larger than that at which an adsorption equilibrium condition is established in the gas sensor so that a sample concentration in the gas sensor is maintained at least at a level at which adsorption is saturated.

2. The method as claimed in claim 1, wherein the sample contains a second compound labelled with stable isotopes, and further comprising, before supplying said first compound, continuously separating respective stable isotope labelled components of said second compound from each other, and converting chemical forms of separated, stable isotope labelled components into those suitable to be spectroscopically sensed by the microwave spectroscope.

3. The method as claimed in claim 1, wherein the flow rate of said first compound is maintained substantially constant.

4. The method as claimed in claim 3, wherein said first compound is mixed at a predetermined ratio with an inert gas in a bomb from which a mixture is supplied to said gas flowing through said gas sensor.

* * * * *